United States Patent [19]

Meilland

[11] Plant 4,682

[45] Apr. 7, 1981

[54] MINIATURE ROSE PLANT—MEIJIKATAR VARIETY

[75] Inventor: Marie L. Meilland, Antibes, France

[73] Assignee: The Conard-Pyle Company, West Grove, Pa.

[21] Appl. No.: 102,417

[22] Filed: Dec. 11, 1979

[30] Foreign Application Priority Data

Jan. 21, 1979 [DK] Denmark ..... 1004/79

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Burns, Doane, Swecker & Mathis

[57] ABSTRACT

A new and distinct variety of rose plant of the Miniature Class is provided having double flowers which are brilliant vermillion red in color. The seed parent of the new variety was the variety Meichanso and the pollen parent was obtained by the crossing of the variety Meidacinu and the variety Duchess of Windsor.

16 Drawing Figures

SUMMARY OF THE INVENTION

The object of the present invention is to provide a new variety of rose plant of the Miniature Class having compact and regular vegetation which is distinguished from prior varieties by the following characteristics:

(1) from the physical point of view, the plant with brownish green adult wood is bushy and produces double flowers of attractive form which are brilliant vermillion red in color having petals of good substance; and (2) from the biological point of view has vigorous vegetation, abundantly forms flowers of long duration having petals which drop off cleanly and average resistance to diseases.

In view of these characteristics the new variety meets the needs of the horticultural industry for all purposes, and particularly is suited for ornamentation in parks and gardens.

The new variety was created by artificial pollination whereby two genitors which previously had been studied for the possession of the characteristics sought in the new variety were combined.

The seed parent of the new variety was the variety Meichanso and the pollen parent was obtained by the crossing of the variety Meidacinu with the variety Duchess of Windsor.

The parentage of the new variety may be expressed as follows:

Meichanso × (Meidacinu × Duchess of Windsor)

The seeds resulting from the above pollination were sown and 145 plantlets were obtained which were physically and biologically different from each other. Selective study resulted in the identification of a single plant of the new variety. Extensive testing has confirmed the behavior and characteristics of the new variety. A miniature plant was produced having attractive unique brilliant red flowers of long duration which were formed in abundance. This plant was particularly adapted for pot forcing and exhibited compact and regular vegetation.

The characteristics and properties of the new variety obtained as indicated above are strictly transmissible by asexual propagation, e.g. by grafting a bud or eye. The rose plant of the new variety has been designated the Meijikatar variety.

BRIEF DESCRIPTION OF THE PHOTOGRAPH

The accompanying photograph shows as nearly true as it is reasonably possible to make the same in a color illustration of this character, typical specimens of plant parts of the new variety cultivated in outdoor fields at the Cannet des Maures, Var, France, illustrated in:

FIG. 1 — a specimen of a young shoot;

FIG. 2 — a specimen of a bud before the opening of the sepals;

FIG. 3 — a specimen of a bud at the opening of the sepals;

FIG. 4 — a specimen of the bud at the opening of the petals;

FIG. 5 — a specimen of the flower in course of opening;

FIG. 6 — a specimen of the fully opened flower—plan view—obverse.

FIG. 7 — a specimen of the fully opened flower—plan view—reverse;

FIG. 8 — a specimen of the flower at the end of the blooming stage—plan view—obverse;

FIG. 9 — a specimen of the flower at the end of the blooming stage—plan view—reverse;

FIG. 10 — a specimen of the receptacle showing the arrangement of the stamens;

FIG. 11 — a specimen of the receptacle showing the arrangement of the pistils (stamens removed);

FIG. 12 — a specimen of a flowering stem;

FIG. 13 — a specimen of a main branch;

FIG. 14 — a specimen of a leaf with three leaflets —upper surface;

FIG. 15 — a specimen of a leaf with seven leaflets —upper surface; and

FIG. 16 — a specimen of a leaf with five leaflets —upper surface.

DETAILED DESCRIPTION

Figures 1, 2, 3, 4, 5, 6, 7, 8, 9, 10, 11, 12, 13, 14, 15, 16:
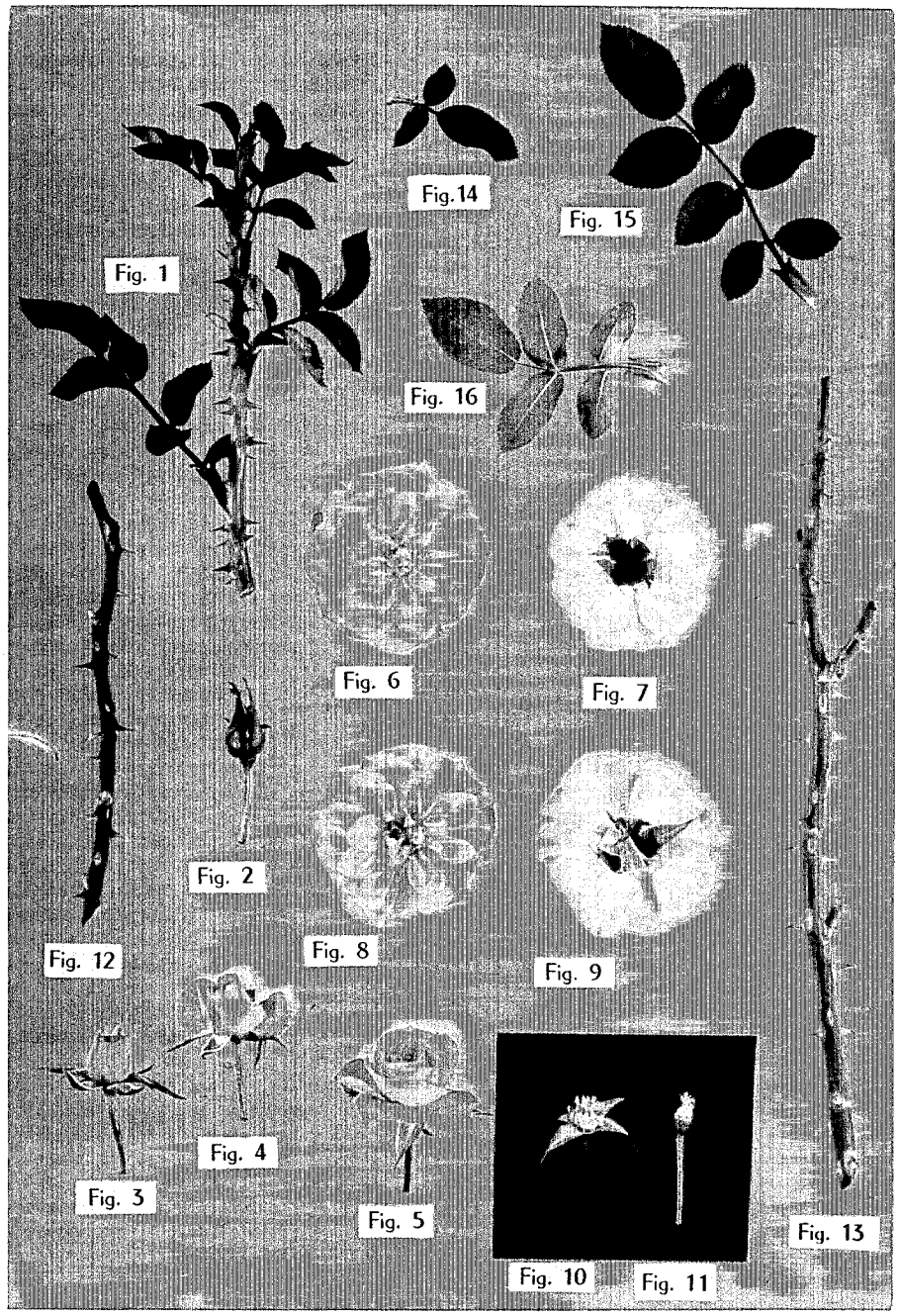

The plants described were grown in outdoor fields at the Cannet des Maures, Var, France.

The chart used in the identification of the colors is that of the Royal Horticultural Society (R.H.S. Colour Chart). The terminology preceding the numbered references has been added to designate in common terms, the corresponding colors.

Class: Miniature.

Plant:

*Height.*—30 cm. on average.

*Habit.*—Bushy.

Branches:

*Color.*—Young stems: Light green, 144A (yellow-green group) with a somewhat reddish shading. Mature wood: Brownish green, 146A (yellow-green group).

*Thorns.*—Shape: Upper edge: Straight and quite pointed. Under edge: Lightly concave. Size: Medium. Quantity: Quite plentiful. Color: On young stems: Reddish On mature wood: Straw color then becoming tobacco colored.

Leaves:

*Stipules.*—Quite straight and linear, furrowed and reddish brown (young leaves).

*Petioles.*—Upper surface: Medium green (adult foliage — sides more or less glandular). Under surface: Reddish (young foliage), light green (adult foliage). This side carries several small hooked thorns.

*Leaflets.*—Number: 3-5-7 (quite often). Shape: Elliptic — lightly lanceolate. Seration: Simple and regular. Texture: Rugged. General overall aspect: Small leaves, dense and dull colored. Color: Young foliage: Upper surface: Dark green 147A (yellow-green group). Under surface: Average green 147B (yellow-green group). Color: Adult foliage: Upper surface: Bronzish green 146A (yellow-green group). Under surface: Light green 147C (yellow-green group).

Inflorescence:

*Number of flowers.*—1 to 3 flowers per stem.

*Peduncle.*—Straight, rigid, lightly spotted reddish brown. It is slightly glandular and carries several small hooked thorns. It is sometimes very lightly creviced. Length: 2.3 cm. on average.

*Sepals.*—Exterior surface: Greenish exhibiting somewhat reddish spots. Interior surfaces: Light green exhibiting to some extent reddish spots and more or less glandular. The exterior sepals have slightly appendicular sides.

*Bud.*—Shape: Conical at the time of the opening of the sepals. Length: 1.1 cm. on average not counting the calyx. Size: Small. Color: At the point of opening: Interior surface: Brilliant vermillion red 44A (red group). Exterior surface: Vermillion red 44B (red group).

*Flower.*—Form: Double. Diameter: 4.8 cm. on average. Color: at point of opening: Upper surface: Brilliant red vermillion 44A (red group). Under surface: Red vermillion 44C (red group). Color: During course of opening: Upper surface: Brilliant red vermillion 44A (red group). Under surface: Red vermillion 44C (red group). Color: When fully open: Upper surface: Brilliant red vermillion 44B (red group). Under surface: Red vermillion 44C (red group). Scent: Very light. Length of life of the bloom: Very long. Corolla: Petals. Texture: Consistent. Form: Well rounded, slightly flattened with a small point at the summit. The petals become cuneiform at the center and have a tendency to refold back from themselves. Number: 40 on average, as well as 12 to 15 petals which are not completely formed at the center of the bloom. The petals fall cleanly after the normal life of the bloom is finished. Stamens: Number: 49 on average. Anthers: Normal, yellow. Pistils: Number: 36 on average. Stigmas: Normal, yellowish. Styles: Free, straw colored and somewhat fushia at the tip, more or less twisted and covered with hairlets; irregular in height. Receptacle: Light green, more or less spotted with reddish brown; at the point of the dehiscence of the anthers and from a longitudinal section the receptacle is very straight and in the form of a funnel.

Developement:

*Vegetation.*—Vigorous.

*Blossoming.*—Abundant.

*Fruiting ability.*—Very weak.

*Resistence to frost.*—Normal.

*Resistance to diseases.*—Good.

I claim:

1. A new and distinct variety of Miniature rose plant characterized by the fact that:

from the physical point of view, the plant with brownish green adult wood is bushy and produces double flowers of attractive form which are brilliant vermillion red in color having petals of good substance; and from the biological point of view has vigorous vegetation, abundantly forms flowers of long duration, having petals which drop off cleanly, and average resistance to diseases;

substantially as shown and described.

* * * * *